United States Patent [19]

Kogo

[11] Patent Number: 4,809,698
[45] Date of Patent: Mar. 7, 1989

[54] TRANSCUTANEOUS BLOOD GAS SENSOR

[75] Inventor: Katsuyuki Kogo, Osaka, Japan

[73] Assignee: Sumitomo Electric Industries, Ltd., Osaka, Japan

[21] Appl. No.: 128,396

[22] Filed: Dec. 2, 1987

[30] Foreign Application Priority Data

Dec. 5, 1986 [JP] Japan ................. 61-291358

[51] Int. Cl.⁴ .............................................. A61B 5/00
[52] U.S. Cl. .................................. 128/632; 128/637; 204/415
[58] Field of Search ............... 128/632, 635, 637, 639; 204/403, 415

[56] References Cited

U.S. PATENT DOCUMENTS

| 3,682,159 | 8/1972 | Imredy et al. | 204/415 |
| 4,197,853 | 4/1980 | Parker | 128/635 |
| 4,432,365 | 2/1984 | Leist | 128/635 |
| 4,624,261 | 11/1986 | Holscher | 128/639 |

FOREIGN PATENT DOCUMENTS

| 0077054 | 4/1983 | European Pat. Off. |
| 2919118 | 11/1979 | Fed. Rep. of Germany |
| 3507183 | 3/1986 | Fed. Rep. of Germany |
| 31220 | 9/1984 | Japan |

Primary Examiner—Edward M. Coven
Assistant Examiner—Randy Citrin
Attorney, Agent, or Firm—W. G. Fasse; D. H. Kane, Jr.

[57] ABSTRACT

A transcutaneous blood gas sensor has a sensor housing with a central projection, a ring-shaped collar to be attached to the skin and a membrane holder having a membrane stretcher hole. The central projection of the sensor housing fits into the stretcher hole for holding and retaining a membrane in position across the membrane stretcher hole whereby a ring zone of the membrane is clamped between the membrane holder and the ring-shaped collar. The central projection of the sensor body has a spherical end surface, whose radius of spherical curvature is at least twice and not more than six times the inner diameter of the membrane stretcher hole. The spherical end surface contacts a central membrane portion.

6 Claims, 6 Drawing Sheets

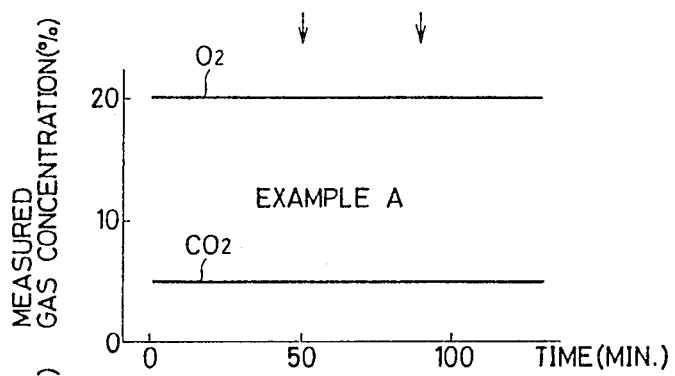
FIG.5 EXAMPLE A
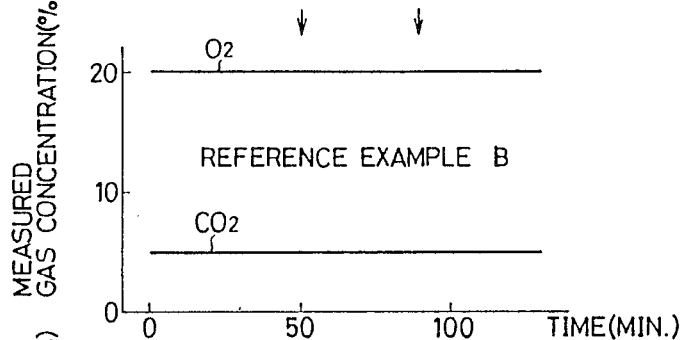
FIG.6 REFERENCE EXAMPLE B
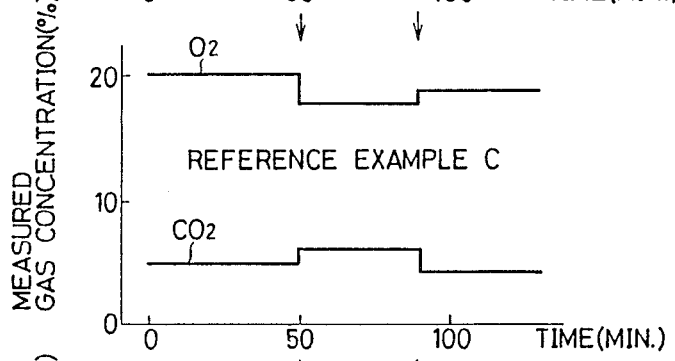
FIG.7 REFERENCE EXAMPLE C
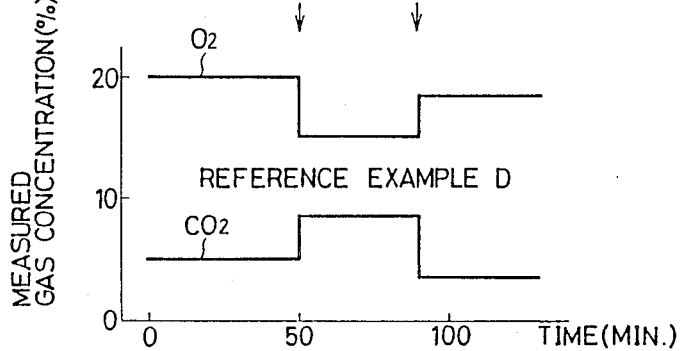
FIG.8 REFERENCE EXAMPLE D

TRANSCUTANEOUS BLOOD GAS SENSOR

BACKGROUND OF THE INVENTION

1. Field of the Invention

The present invention relates to a transcutaneous blood gas sensor, which can continuously measure a gas concentration in the blood of the human body by attaching a sensor onto the skin.

2. Description of the Art

A well-known conventional transcutaneous blood gas sensor is disclosed in Japanese Utility Model Publication Gazette No. 31220/1984, for example. FIG. 11 is a sectional view showing an example of such a conventional transcutaneous blood gas sensor. The conventional gas sensor as shown in FIG. 11 has a sensor housing 1, a membrane holder 4 and a ring-shaped collar 6. The membrane holder 4 is located between the sensor housing 1 and the ring-shaped collar 6, which is threadedly connected to the sensor housing 1 to mount the membrane holder 4 on the sensor housing 1. The sensor housing 1 is provided in its periphery with a threaded part 8 and the ring-shaped collar 6 is provided in its inner periphery with a threaded part 7 for such threaded connection.

The sensor housing 1 is further provided, in its central portion, with a central projection 9, which has a flat end surface 12. The membrane holder 4 has in its central portion, a membrane stretcher hole 10 which is sized to fittingly receive the central projection 9 of the sensor housing 1, and a membrane 3 is held between the periphery of the membrane stretcher hole 10 and that of a ring part opening 5 of the ring-shaped collar 6. The membrane holder 4 and the ring-shaped collar 6 are fastened to each other at a circumferential irregular part 16.

As shown in prior art FIG. 12, the sensor housing 1 is threadedly connected with the ring-shaped collar 6 so as to retain an electrolytic solution in chamber 20 between the membrane 3 and the end surface 12 of the central projection 9. In the conventional gas sensor of the aforementioned structure, however, the electrolytic solution is gradually collected and an excessive quantity of electrolytic solution is retained. The electrolytic solution thus excessively retained is moved when the membrane touches the skin in attachment/detachment of the sensor to/from the human body, whereby the values measured by the gas sensor fluctuate extremely and in most cases do not to return to the original value. Hence, a calibration must be performed repeatedly.

Prior art FIG. 13 shows a jig 17 for threaded connection, which jig is well known as means for solving such a problem. Referring to FIG. 13, the jig 17 is engageable/disengageable with/from the ring-shaped collar 6, and has an elastic member 18 in a part located in the ring part opening 5 of the ring-shaped collar 6. The elastic member 18, being made of rubber or sponge, is adapted to press the membrane 3 when the sensor housing 1 is threadedly connected with the ring-shaped collar 6. The membrane 3 is so pressed in threaded connection that no excessive electrolytic solution is retained between the membrane 3 and the end surface 12 of the central projection 9.

In such a method, however, the jig for threaded connection must be engaged/disengaged with/from the sensor for replacement of the membrane, whereby operation for replacing the membrane is complicated.

SUMMARY OF THE INVENTION

An object of the present invention is to provide a transcutaneous blood gas sensor, which can suitably adjust the volume of an electrolytic solution retained between a sensor housing and a membrane while uniformalizing thickness of the layer of the electrolytic solution without employing a specific jig for threadedly connecting the membrane holder to the sensor housing.

In the transcutaneous blood gas sensor according to the present invention, a central projection of the sensor housing has a spherical end surface, whose radius is at least twice and not more than six times the inner diameter of a membrane stretcher hole.

According to the present invention, the electrolytic solution can be retained in suitable volume between the sensor housing and the membrane and the layer of the electrolytic solution can be uniformalized in thickness without employing a jig for threaded connection such as that in the prior art. Thus, no extreme fluctuation of the measured value is caused even if the membrane is touched by the skin or the like during measurement, while the measured value can be stabilized in a short time after replacement of the membrane.

These and other objects, features, aspects and advantages of the present invention will become more apparent from the following detailed description of the present invention when taken in conjunction with the accompanying drawings.

BRIEF DESCRIPTION OF THE DRAWINGS

FIG. 5 illustrates the measured value of the gas concentration as a function of time of an Example A of the present invention, in which a spherical end surface of a central projection of a sensor housing has a radius of spherical curvature corresponding to four times the inner diameter of a membrane stretcher hole;

FIG. 6 illustrates the measured value of the gas concentration as a function of time of a Reference Example B, in which a spherical end surface of a central projection of a sensor housing has a radius of spherical curvature corresponding to 1.5 times the inner diameter of a membrane stretcher hole;

FIG. 7 illustrates fluctuation of the measured value of reference example, in which a spherical end surface of a central projection of a sensor housing has a radius of 7 times the inner diameter of a membrane stretcher hole;

FIG. 8 illustrates fluctuation of the measured value of reference example, in which a central projection of a sensor housing has a flat end surface.

DESCRIPTION OF THE PREFERRED EMBODIMENTS

Figure 1:
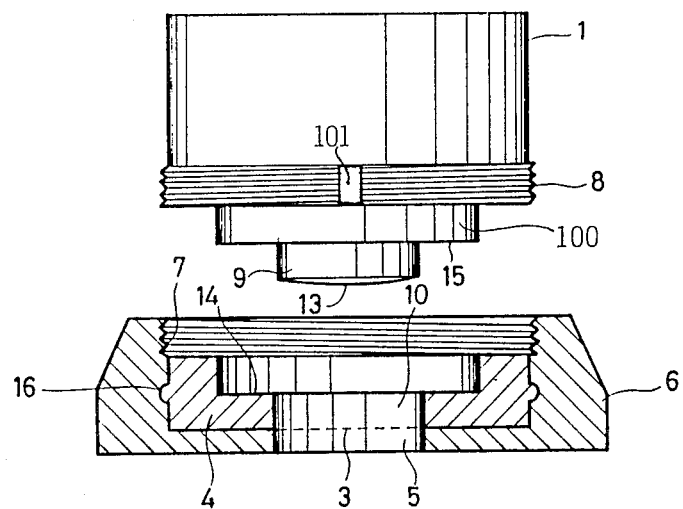
FIG. 1 is a sectional view showing an embodiment of the present invention in a state previous to threaded connection.

An embodiment of the present invention is now described with reference to FIGS. 1 to 3. A membrane holder 4 is provided between a sensor housing 1 and a ring-shaped collar 6, which is threadedly connected to the sensor housing 1 to mount the membrane holder 4 on the sensor housing 1. The sensor housing 1 is provided in its periphery with an outer threading 8 and the ring-shaped collar 6 is provided in its inner peripheral portion with an inner threading 7 for connecting the collar 6 to the housing 1.

The sensor housing 1 is further provided in its central portion with a central projection 9 connected at its upper end through a stepped section 100 to the sensor housing 1. The central projection 9 has an end portion forming a spherical segment having a spherical end surface 13 with a radius of spherical curvature of at least twice and not more than six times the inner diameter of a membrane stretcher hole 10 in the membrane holder 4. The stretcher hole 10 has a given diameter sized to fittingly receive the central projection 9 of the sensor housing 1. A membrane 3 is held between the membrane holder 4 and the ring-shaped collar 6 so that a central portion of the membrane is stretched across the stretcher hole 10 and across an opening 5 of the ring-shaped collar 6. The membrane holder 4 and the ring-shaped collar 6 are fastened to each other at circumferential locking elements 16.

The stepped section 100 has an abutting surface 15 facing downwardly and extending around the central projection 9 of the sensor housing 1. An abutting surface 14 facing upwardly is formed around the membrane stretcher hole 10 of the membrane holder 4. These abutting surfaces 15 and 14 are oppositely brought into contact with each other when the ring-shaped collar 6 and the membrane holder 4 are mounted on the sensor housing 1, thereby to prevent leakage of an electrolytic solution retained in a chamber 20′ formed between the spherical end surface 13 of the central projection 9 and the membrane 3, when the collar 6 has been tightly screwed onto the sensor housing 1.

Figure 2:
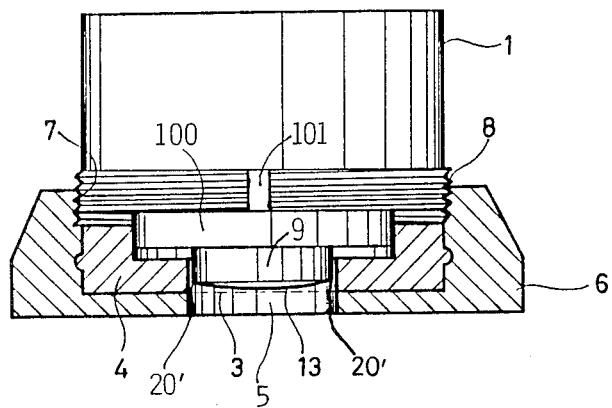
FIG. 2 is a sectional view showing the embodiment of FIG. 1 in an intermediate state of threaded connection.

FIG. 2 is a sectional view showing a state in which the ring-shaped collar 6 is being threadedly connected to the sensor housing 1, but the abutting surfaces 14 and 15 do not contact each other yet. FIG. 3 is a sectional view showing a state after the threaded connection is completed so that the surfaces 14 and 15 contact each other. In operation for making the threaded connection, the spherical end surface 13 is first brought into contact with the membrane 3 as shown in FIG. 2, so that the contact area between the spherical end surface 13 and a central portion of the membrane 3 is gradually enlarged as the end surface 13 is moved downwardly. Thus, the electrolytic solution is gradually circumferentially spread to flow out between the threadings 7 and 8 before the surfaces 14 and 15 contact each other. In order to smooth such outflow of the electrolytic solution, the threading 8 of the sensor housing 1 may be provided with at least one groove 101 which extends across the thread ridge of the threading 8.

Figure 3:
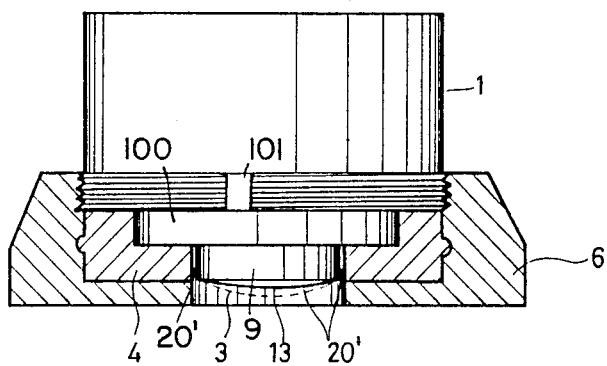
FIG. 3 is a sectional view showing the embodiment of FIG. 1 in a state after threaded connection.

Thus, any excess electrolytic solution is discharged prior to the completion of the threaded connection, whereby no excessive electrolytic surface is retained in the chamber 201 between the membrane 3 and the spherical end surface 13, as shown in FIG. 3. The central portion of the membrane 3 is surrounded by a membrane ring portion extending flat and radially away from the central membrane ring portion, as best seen in FIG. 2. The membrane ring portion is clamped in place between the collar 6 and the holder 4 as best seen in FIG. 3.

According to the present invention, the spherical end surface 13 of the central projection 9 of the sensor housing 1 has a radius of spherical curvature at least twice and not more than six times the inner diameter of the membrane stretcher hole 10 since the effect of circumferentially spreading the electrolytic solution cannot be sufficiently attained if the radius of the spherical end surface is greater than six times the inner diameter of the membrane stretcher hole. On the other hand, the membrane is pressed and expanded by the end surface 13 of the central projection 9 if the radius of spherical curvature is less than twice the inner diameter of hole 10, whereby the gas permeability of the membrane 3 is gradually changed and thereafter a considerable time is required for returning the permeability to a steady state. However, when the teaching of the invention is applied, the measured value of the sensor is stabilized within 30 minutes after the threaded connection is established according to the present invention, in which the radius of spherical curvature of the spherical end surface 13 is at least twice the inner diameter of the membrane stretcher hole 10. Contrary to the foregoing, several hours are required for such stabilization if said radius is smaller than twice the inner diameter of the hole 10.

Figure 4:
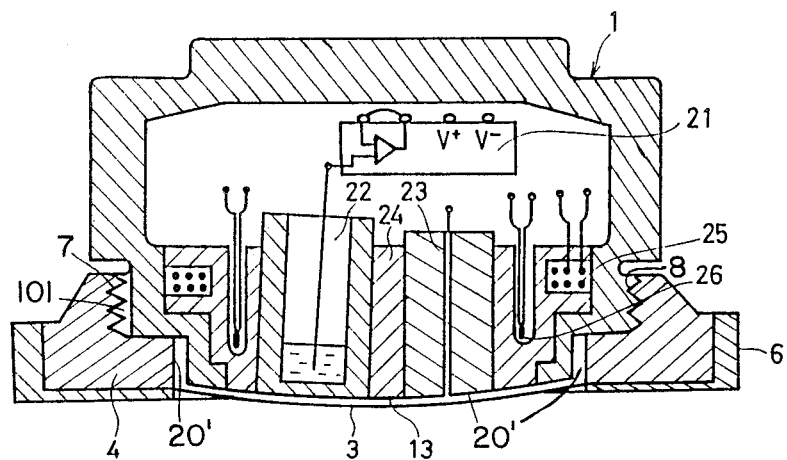
FIG. 4 is a sectional view schematically showing another embodiment of the present invention.

FIG. 4 is a sectional view schematically showing another embodiment (Example A) of the present invention. The measured gas concentration as a function of time of the Invention Example A is shown in FIG. 5. Referring to FIG. 4, a gas sensor as shown in FIG. 4, Example A comprises a preamplifier 21, a pH electrode 22 for measuring carbon dioxide gas, a cathode 23 for measuring oxygen, a silver electrode 24, a heater 25 and a thermistor 26. The other structure of the embodiment of FIG. 4 is similar to that of FIG. 1, and hence a redundant description is omitted. The silver electrode 24 is adapted to serve as a skin heater, an anode for measuring oxygen and a reference electrode for measuring carbon dioxide gas. In the gas sensor of the invention as shown in FIG. 4, a membrane stretcher hole of a membrane holder 4 was 10 mm in inner diameter. A spherical end surface 13 of a central projection of a sensor housing was 40 mm in radius, which is within the scope of the present invention represented by Example A. For the purpose of comparison, gas sensors having spherical end surfaces with an inner diameter of 15 mm and 70 mm respectively, which are outside of the scope of the present invention, and a gas sensor including a central projection having a flat end surface were prepared as Reference Examples B, C and D, respectively.

These four types of gas sensors Invention Example A and Reference Examples B, C, D were left in a gas atmosphere composed of 5 percent of $CO_2$, 20 percent of $O_2$ and 75 percent of $N_2$, to measure the $CO_2$ and $O_2$ concentrations. The $CO_2$ concentration of 5 percent and the $O_2$ concentration of 20 percent were set prior to starting the recording of data, and the membranes of the gas sensors were touched by a finger upon lapses of 50 minutes and 90 minutes after the start of recording data. FIGS. 5 to 8 illustrates the states of fluctuation in measured values (downward arrows indicate finger touches). In Reference Example B as shown in FIG. 6 and in Example A of the invention as shown in FIG. 5, substantially no fluctuation of the measured values was recognized in response to finger touches on the membranes. On the other hand, the measured values fluctuated extremely when the membranes were touched in reference examples C and D as shown in FIGS. 7 and 8.

Figure 9:
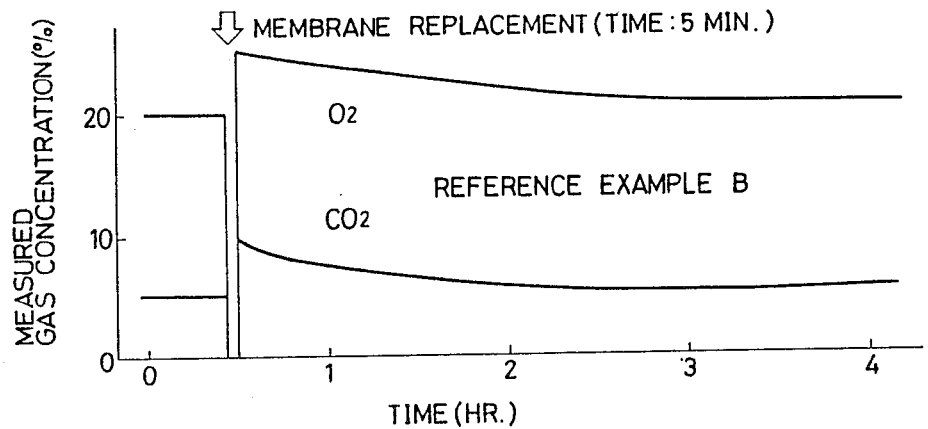
FIG. 9 illustrates fluctuations of the measured value of the Reference Example B as shown in FIG. 6 after replacement of the membrane.
Figure 10:
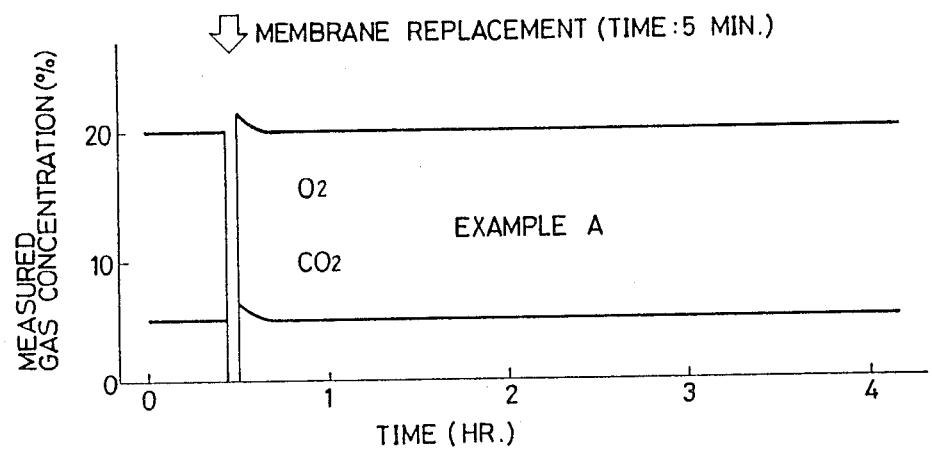
FIG. 10 illustrates fluctuation in the measured value of the Invention Example A as shown in FIG. 5 after replacement of the membrane.
Figure 11:
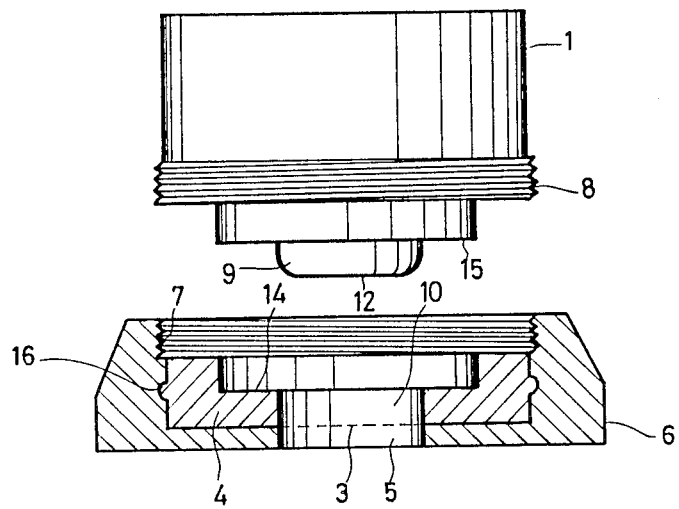
FIG. 11 is a sectional view showing a conventional gas sensor in a state previous to threaded connection.
Figure 12:
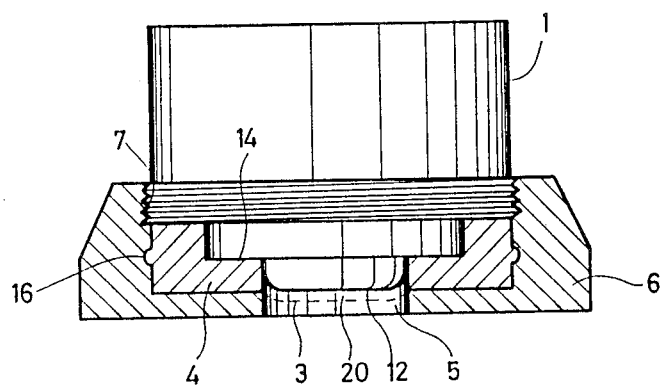
FIG. 12 is a sectional view showing the conventional gas sensor in a state after threaded connection.
Figure 13:
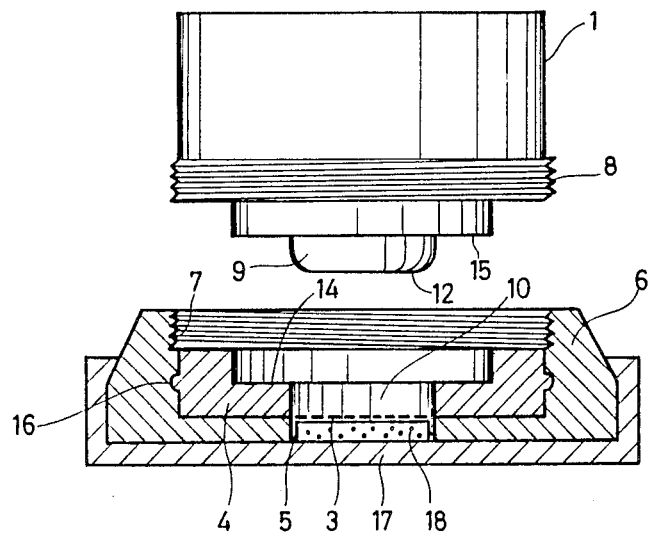
FIG. 13 is a sectional view for illustrating a jig generally employed for threaded connection.

Fluctuation of the measured values in replacement membranes were checked with respect to Invention Example A and Reference Example B, having measured values which did not fluctuate in response to being touched by a finger, i.e., the measured values were stable. However, FIGS. 9 and 10 show the results of measurements of Reference Example B and Invention Example A respectively. It is clear from FIGS. 9 and 10, several hours were required for stabilization of the measured value after replacement of the membrane in the Reference Example B, having a central projection with a spherical end surface of a radius outside of the scope of the present invention, while the measured value was stabilized within about 10 minutes after replacement of the membrane in the Invention Example A, having a central projection with a spherical end surface of a radius of a spherical curvature within the scope of the present invention. Thus, it is clear that the time required for stabilization of the measured value after a membrane replacement is reduced as the radius of the spherical end surface of the central projection is increased as taught by the invention. The measured value is preferably stabilized within about 30 minutes in practice, and hence the spherical end surface of the central projection must have a radius of spherical curvature of greater than twice the inner diameter of the membrane stretcher hole.

As hereinabove described, the spherical end surface of the central projection according to the invention has a radius of spherical curvature of at least twice and not more than six times the inner diameter of the membrane stretcher hole, so that the measured value does not fluctuate even if the membrane is touched by a finger and the measured value can be stabilized in a short time after replacement of the membrane. The fluctuation in the measured value caused by a touch to the membrane comes into question particularly when the inner diameter of the membrane stretcher hole is in excess of 4 mm, since the membrane is frequently touched by the skin or the like in this case.

The excessive electrolytic solution must be discharged through the threaded connection of the sensor body and the ring-shaped collar. In order to ensure such outflow of the electrolytic solution, the threaded part of the sensor housing may be provided with grooves 101 as shown for example at 101 in FIG. 2 which extend across the threaded ridges, as hereinabove described. Although the membrane holder and the ring-shaped collar are threadedly mounted on the sensor housing in the aforementioned embodiment, the method of such mounting is not restricted to a threaded connection, according to the present invention, but another mounting method such as fastening can be employed.

While the membrane holder 4 is assembled as a ring-shaped collar in the aforementioned embodiment, the present invention is not restricted to such a structure. Further, although the abutting surfaces are provided in the peripheries of the central projection of the sensor housing and the membrane stretcher hole of the membrane holder, it is obvious that such abutting surfaces may be omitted.

The gas measuring part of the sensor body may be adapted to measure either oxygen gas or carbon dioxide, or any other gas.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A transcutaneous blood gas sensor comprising: a membrane, sensor means for sensing gas, said sensor means comprising a sensor housing with a central projection (9) having a portion forming a spherical segment for contacting said membrane, a ring-shaped collar to be attached to a patient's skin, a membrane holder having a membrane stretcher hole with a given hole diameter for receiving said central projection of said sensor housing, said membrane holder cooperating with said ring-shaped collar for retaining said membrane across said membrane stretcher hole between said membrane holder and said ring-shaped collar, said spherical segment having a spherical end surface (13) with a radius of spherical curvature corresponding in length to a multiple of said given hole diameter of said stretcher hole, said multiple being within the range of at least two to not more than six, said spherical end surface (13), said membrane (3), a peripheral surface of said central projection (9) and an inner surface of said membrane stretcher hole forming a chamber (20') for holding electrolytic solution, said chamber (20') having a chamber bottom portion between said membrane and said spherical end surface and a chamber ring portion between said membrane holder (4) and said central projection (9) so that said central projection (9) is surrounded by a sufficient volume of electrolytic solution, means for operatively holding said membrane holder (4) in place, and groove means (101) connected to said chamber (20') for providing a release path for excessive electrolytic solution out of said chamber (20') when said sensor housing, said membrane holder and said ring shaped collar are being brought into an assembled position relative to one another, and means for closing said release path when said assembled position has been established.

2. The transcutaneous blood gas sensor of claim 1, wherein said given hole diameter of said membrane stretcher hole is at least 4 mm.

3. The transcutaneous blood gas sensor of claim 1, wherein said means for closing said release path comprise a stepped connecting section (100) in said sensor housing, said stepped connecting section including a first abutting ring surface (15) around said central projection (9), said membrane holder (4) having a second abutting ring surface (14) surrounding said stretcher hole, said first and second abutting surfaces (15, 14) contacting each other to close said release path when said assembled position has been established.

4. The transcutaneous blood gas sensor of claim 1, wherein said membrane has a central portion stretched across said stretcher hole and a ring portion surrounding said central membrane portion, said membrane ring portion extending radially and flat away from said central membrane portion, said membrane ring portion being clamped between said ring-shaped collar and said membrane holder.

5. The transcutaneous blood gas sensor of claim 1, wherein said means for operatively holding said membrane holder in place comprise threading means provided on said sensor housing and on said ring-shaped collar, whereby said membrane holder is held in place between said sensor housing and said ring-shaped collar.

6. The transcutaneous blood gas sensor of claim 1, wherein said means for operatively holding said membrane holder in place comprise threading means provided on said sensor housing and on said membrane holder, whereby said membrane holder is threaded to said sensor housing, and wherein said ring-shaped collar is secured to said membrane holder.

* * * * *